United States Patent [19]

Huber

[11] Patent Number: Plant 7,283

[45] Date of Patent: Jul. 31, 1990

[54] PRIMOCANE RASPBERRY NAMED "PER HUB"

[75] Inventor: Tony Huber, Laval, Canada

[73] Assignee: W. H. Perron et Cie. LTEE, Quebec, Canada

[21] Appl. No.: 178,432

[22] Filed: Apr. 6, 1988

[51] Int. Cl.[5] ..... A01H 5/00

[52] U.S. Cl. ..... Plt./46

[58] Field of Search ..... Plt./46

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A raspberry variety named "Per Hub" combines the characteristics of primocane fruiting, vigorous canes and growth, good size and taste of fruit, hardiness, adaptation and good resistance to diseases and insects. Plants of the Per Hub variety product conical berries approximately 35 mm in length and 25 mm in diameter. Per Hub compares favorably with the popular Heritage variety, yielding bigger berries with significantly higher sugar content.

3 Drawing Sheets

BACKGROUND OF THE INVENTION

The present invention relates to a new and distinctive cultivar of red raspberry named Per Hub. This cultivar is exceptional for its size, high sugar content, hardiness and resistance to disease and insects.

The Per Hub cultivar of *Rubus idaeus* var. strigosus was produced by crossing the variety Pathfinder, as pollen plant, with the variety Zeva Herbsternte. Both parent varieties are publicly available. Pathfinder was developed at the University of Wisconsin (Madison) and was one of the first available "primocane," or first year-fruiting, varieties. Zeva Herbsternte is a Swiss cultivar known for its fruity aroma. Among the seedlings obtained from the designated cross, the "Per HUB" variety has been found to display the best qualities of both parents. After being propagated from suckers and root cuttings, it has shown itself to be stable.

DESCRIPTION OF THE PHOTOGRAPHS

The appended sheets document the color and other characteristic features of the new cultivar.

The first sheet shows a mature raspberry bush of the Per Hub variety.

The second sheet shows a branch of the variety which contains both ripe and maturing raspberries.

The third sheet shows mature raspberry fruit of the variety, with unripened fruit in the background.

DESCRIPTION OF THE INVENTION

The new variety of the present invention is characterized by primocane fruiting, vigorous canes and growth, good size, tasty fruits and hardiness. The plants display wide adaptation and good resistance to disease and insects. It is an an autumn-bearing variety.

I have reproduced this new variety both by root cuttings of suckers and by tissue culturing. The latter propagation method utilizes artificial nutrient media under aspetic (pathogen-free) conditions in controlled laboratory environments. Because it guarantees virus-free plants, propagation by tissue culturing is preferred in the context of the present invention.

In general terms, tissue culture is divided into four stages of development. The first stage (stage 1) entails establishing a sterile culture of a portion (explant) of the stock plant. During stage 2 there is a stimulation of multiple shoot development, which usually involves transferring cultured material to a medium with containing levels of the plant hormone cytokinin. Stage 3 involves preparing the cultured material for removal from culture, a process that typically entails exposing the material to increased auxin levels to initiate roots on shoots which were multiplied in stage 2. Finally, cloned plants are adapted to greenhouse conditions during stage 4, in the course of which there is always a gradual reduction of humidity until the plants are hardened off.

With regard to the Per Hub cultivar, stage 4 usually includes rooting, that is, the variety of the present invention can be rooted directly in stage 4; accordingly, stage 3 is optional. The specific details of raspberry propagation are otherwise conventional, as disclosed, for example, by Anderson, "Tissue Culture Propagation of Red Raspberry," In Vitro 15 (3): 177 (1979), and "Tissue Culture Propagation of Red and Black Raspberries. *Rubus idaeus* and *R. occidentalis,*" *Acta Hort.* 112: 13–20 (1980); by Pyott and Converse, "In Vitro Propagation of Heat-Treated Raspberry Clones," *Hort. Sci.* 16(3): 308–309 (1981); and by Snir, "Micropropagation of Red Raspberry,"*Scienta Hort.* 14: 139–143 (1981), the respective contents of which documents are hereby incorporated by reference.

The fruits of the Per Hub cultivar are conical, averaging about 35 mm in length and 25 mm in diameter. The weight of one berry ranges from about 1.7 grams to about 6.7 grams with the average weight of one berry being about 3.4 grams. Laboratory analysis show these fruits to have high sugar and pectin contents, and they are excellent for fresh consumption, freezing, and for jam, jelly or syrup production. Per Hub is well-suited for roadside markets, "pick-your-own" farms and home gardens.

Per Hub compares favorably with the Heritage variety, also popular and widely grown in the same geographic zone. Per Hub has bigger berries than Heritage, with significantly higher sugar content.

Fully ripe raspberries of the new variety possess a reddish purple color, corresponding to the range from 46A to 60A of The Royal Horticultural Society (R.H.S.) Colour Chart. The actual fruit coloration depends on the ripening stage, as well as on light exposure and other factors. Its leaves are of a green color, corresponding most closely to R.H.S. color 137B. (The color evaluations described herein were made in St. Eustache, Quebec, Canada, on the morning of Aug. 24, 1987, at 9:30 a.m. Viewing was effected in direct sunlight under dry, cool conditions, when the temperature was approximately 60° F.).

The drupelets average about 5 mm in diameter. The seeds have a flattened kidney shape. They average approximately 3 mm in length, 2 mm in width and 1 mm in thickness.

The largest leaves of the variety are basal leaves averaging 18.5 to 24 cm in length and 15.0 to 20 cm in width, measured from the base of the petiole. The sizes of the leaf decrease at each higher position on the stem. The blossom date extends from about June 20 until frost (on new canes), producing white blossoms.

Per Hub is a fall-bearing variety, and bears until frost. Accordingly, it is not possible to count the total number of fruit per cane, as this largely varies with the length of the season. Each cluster is formed of 2 to 8 berries. A cluster is considered the stem that bears only fruits and that originates at one leaf axil.

The firmness of the mature fruit (Newtons) has been measured at 30.5±7.4. Juiciness has been measured at 81.6%±2.3%.

The results of chemical analyses of Per Hub, indicating its humidity (percent of water), pH, Brix value (percent of soluble solids) and titrating acidity (percent of citric acid in the fruit), are set forth in the following table, along with corresponding values of a typical cultivated variety.

TABLE

| | pH | Acidity (%) citric acid | Brix Value | Humidity (%) |
|---|---|---|---|---|
| Per Hub Variety | 3.36 | 1.44 | 7.5 | 12.85 |
| Typical Cultivated Variety (c.v. Malling Promise)* | 3.37 | 1.65 | 8.9 | 11.20 |

*Data taken from "The Suitability of Cultivars of Raspberries for Q Freezing," Fruit Science Reports 9 (No. 2):59 (1982), at Tables 4, and 6.
The authors evaluated ten varieties and identified Malling Promise as a standard.

Canes are stocky, bristly and initially green-colored, turning purplish in the first season then becoming brown and woody the year after. They reach about 4 to 5 feet in height, and about 12 to 15 canes are produced per plant in the second year.

As a vigorous, primocane variety, Per Hub canes do not need support. Lateral branches are found at growing heights in the range of 18 imches (45cm) or lower.

In northern temperate climates, fruits are first produced around July on previous year's canes, but these fruits are smaller. Primocane fruiting starts during August to reach maximum fruiting production during September. This fruiting persists until frost. Primocane fruits are larger.

Per Hub can be pruned back to ground level late in the fall if no early fruiting is desired. If earlier production is desirable, strong one year-old canes can be preserved and pruned back to 30 inches (75 cm). The variety bears abundant, huge fruits during its long fruiting season, and is preferably fertilized twice a year (in early spring and mid-summer). The leaves of Per Hub are compound, comprised of three ovate leaflets which have dentate margins and which are pubescent beneath.

I claim:

1. A new and distinct cultivar of *Rubus idaeus* var. strigosus, named Per Hub, as herein shown and described, characterized particularly as to uniqueness by the combined characteristics of primocane fruiting, vigorous canes and growth, good size and taste of fruit, hardiness, adaptation and good resistance to diseases and insects, producing conical berries approximately 35 mm in length and 25 mm in diameter.

* * * * *

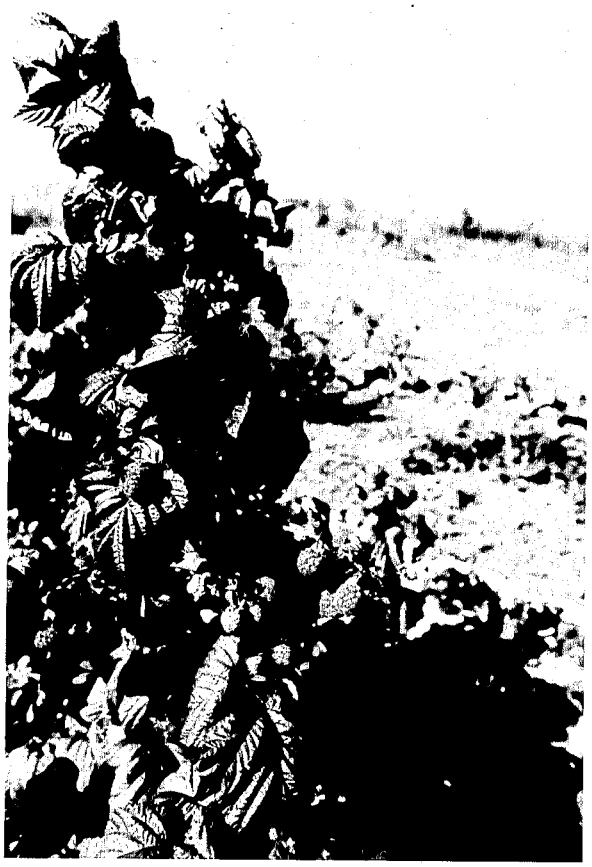

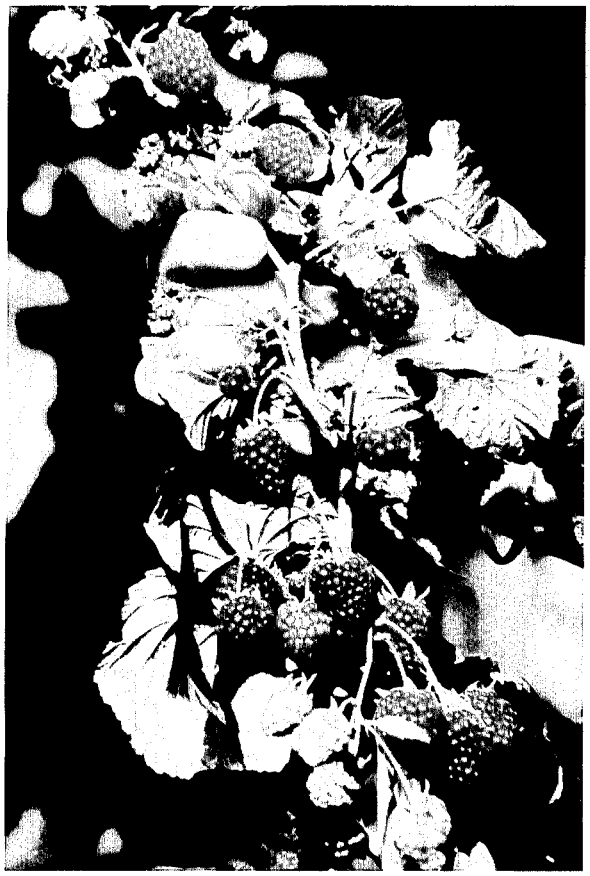

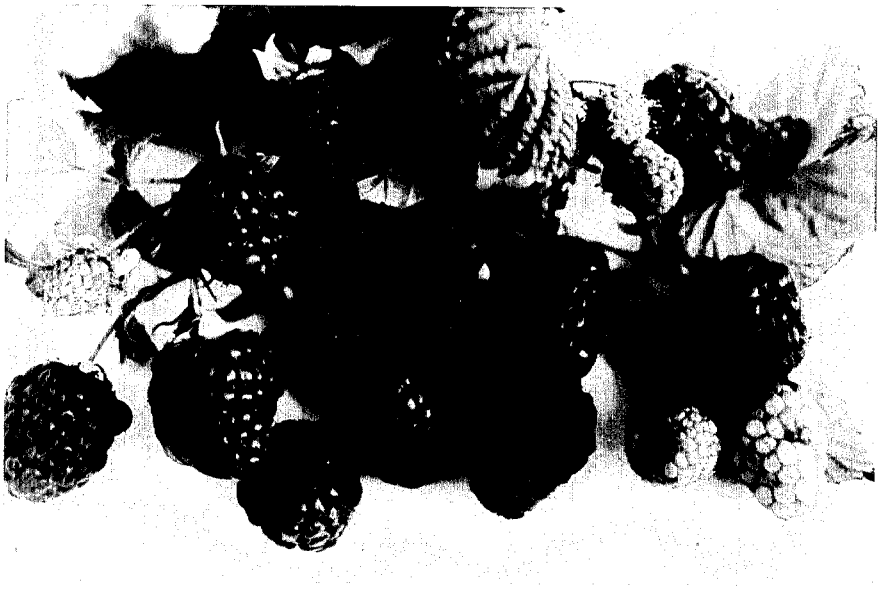

UNITED STATES PATENT AND TRADEMARK OFFICE

CERTIFICATE OF CORRECTION

PATENT NO. : Plant 7,283

DATED : July 31, 1990

INVENTOR(S) : Tony Huber

It is certified that error appears in the above-identified patent and that said Letters Patent is hereby corrected as shown below:

Column 1, line 38, change "aspetic" to -- aseptic --.

Signed and Sealed this

Second Day of June, 1992

*Attest:*

*Attesting Officer*

DOUGLAS B. COMER

*Acting Commissioner of Patents and Trademarks*